US007225022B2

(12) United States Patent
Anderson et al.

(10) Patent No.: US 7,225,022 B2
(45) Date of Patent: May 29, 2007

(54) METHOD OF OPTIMIZING PATIENT OUTCOME FROM CARDIAC RESYNCHRONIZATION THERAPY

(75) Inventors: Stephen T. Anderson, North Oaks, MN (US); Dean J. MacCarter, Englewood, CO (US)

(73) Assignee: CRA Associates, Ltd., North Oaks, MN (US)

(*) Notice: Subject to any disclaimer, the term of this patent is extended or adjusted under 35 U.S.C. 154(b) by 440 days.

(21) Appl. No.: 10/797,948

(22) Filed: Mar. 11, 2004

(65) Prior Publication Data

US 2004/0181260 A1  Sep. 16, 2004

Related U.S. Application Data

(60) Provisional application No. 60/453,938, filed on Mar. 12, 2003.

(51) Int. Cl.
*A61N 1/365* (2006.01)

(52) U.S. Cl. .............................. 607/18; 607/17; 607/19; 607/20; 607/23; 607/24

(58) Field of Classification Search ................. 607/17, 607/18, 20, 23, 24, 1, 2, 9; 600/508, 513, 600/526, 531, 532, 481, 483, 484, 485, 529
See application file for complete search history.

(56) References Cited

U.S. PATENT DOCUMENTS

| 4,463,764 | A | * | 8/1984 | Anderson et al. | ........... 600/532 |
|---|---|---|---|---|---|
| 5,540,727 | A | * | 7/1996 | Tockman et al. | .............. 607/17 |
| 6,174,289 | B1 | * | 1/2001 | Binder | ....................... 600/532 |
| 6,258,038 | B1 | * | 7/2001 | Haryadi et al. | ............. 600/483 |
| 6,517,496 | B1 | * | 2/2003 | Mault | .......................... 600/532 |
| 6,985,772 | B2 | * | 1/2006 | Holmstrom et al. | ........... 607/9 |
| 2003/0097158 | A1 | * | 5/2003 | Belalcazar | .................... 607/32 |
| 2005/0027323 | A1 | * | 2/2005 | Mulligan et al. | ............. 607/18 |

* cited by examiner

*Primary Examiner*—Robert Pezzuto
*Assistant Examiner*—Eugene Wu
(74) *Attorney, Agent, or Firm*—Nikolai & Mersereau, P.A.; C. G. Mersereau

(57) ABSTRACT

A method of data management for optimizing the patient outcome from the provision of cardiac resynchronization therapy (CRT) is described. This method describes a process by which sets of dynamic cardiopulmonary dependent variables are measured during steady-state conditions, displayed, and translated into quantitative and qualitative measurements while the independent variables of CRT, device lead placement and atrial-ventricular and interventricular delay settings of bi-ventricular pacemaker systems, are altered by a physician. In combination with visual observation and computer-assisted ranking of the dependent variables, a physician can utilize the resulting information to render decisions on the optimal choice of the independent variables.

17 Claims, 9 Drawing Sheets

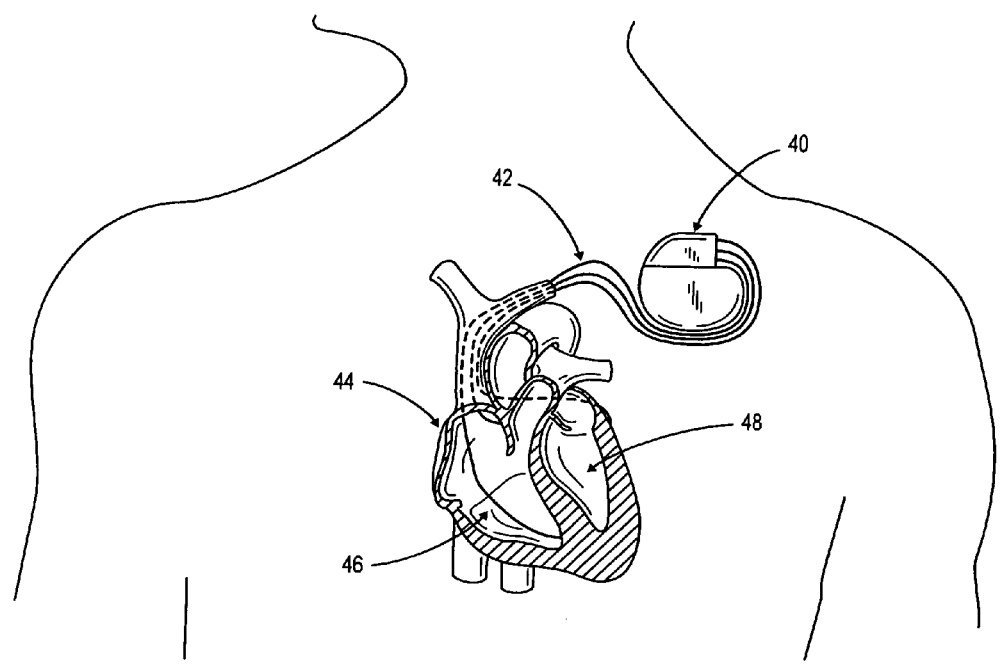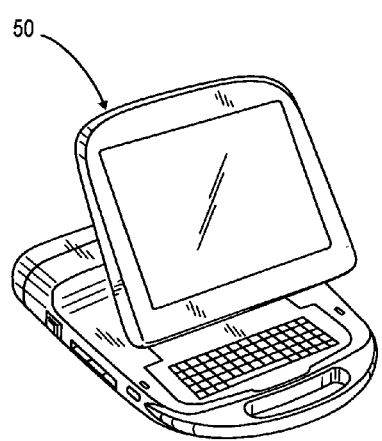
FIG. 2

|  | A V (ms) | V V (ms) |
|---|---|---|
| Minimum | (60) 100 | (66) 10 |
| Average | (62) 140 | (68) 20 |
| Maximum | (64) 180 | (70) 30 |

FIG. 4

Delay Optimization Protocol

| Elapsed Time | System Operator Tasks | Data Processing Tasks |
|---|---|---|
| 0 | Connect Patient to CPX | |
| 1 | Start Treadmill<br>Prestart Measurement<br>Set AV min<br>Start Measurement | Display Variables |
| 3 | Observe Variables<br>Set AV ave | Display Variables<br>Store Variables to AV min |
| 5 | Observe Variables<br>Set AV max | Display Variables<br>Store Variables to AV ave |
| 7 | Observe Variables | Display Variables<br>Store Variables to AV max |
| 8 | Select and Set AV opt<br>Rest Patient (Opt.)<br>Set VV min | Calculate Decision Matrix<br>Print Decision Matrix<br>Print Report Summary |
| 10 | Observe Variables<br>Set VV ave | Display Variables<br>Store Variables to VV min |
| 12 | Observe Variables<br>Set VV max | Display Variables<br>Store Variables to VV ave |
| 14 | Observe Variables | Display Variables<br>Store Variables to VV max |
| 15 | Stop Treadmill<br>Stop Measurement<br>Select and Set VV opt | Calculate Decision Matrix<br>Print Decision Matrix<br>Print Report Summary |

FIG. 5

| Elapsed Time | | | O2 Pulse | EQ CO2 | ETCO2 | Vent. Eff. Slope |
|---|---|---|---|---|---|---|
| Start | | | | | | |
| 1 min | Breath 1 | AV min | 0 | 0 | 0 | 0 |
| | Breath 2 | | 0 | 0 | 0 | 0 |
| | | | 0 | 0 | 0 | 0 |
| | Breath n | | 0 | 0 | 0 | 0 |
| 3 min | Breath 1 | AV ave | 0 | 0 | 0 | 0 |
| | Breath 2 | | 0 | 0 | 0 | 0 |
| | | | 0 | 0 | 0 | 0 |
| | Breath n | | 0 | 0 | 0 | 0 |
| 5 min | Breath 1 | AV max | 0 | 0 | 0 | 0 |
| | Breath 2 | | 0 | 0 | 0 | 0 |
| | | | 0 | 0 | 0 | 0 |
| | Breath n | | 0 | 0 | 0 | 0 |
| 7 min | | | | | | |
| | | | | | | |
| 8 min | Breath 1 | VV min | 0 | 0 | 0 | 0 |
| | Breath 2 | | 0 | 0 | 0 | 0 |
| | | | 0 | 0 | 0 | 0 |
| | Breath n | | 0 | 0 | 0 | 0 |
| 10 min | Breath 1 | VV ave | 0 | 0 | 0 | 0 |
| | Breath 2 | | 0 | 0 | 0 | 0 |
| | | | 0 | 0 | 0 | 0 |
| 12 min | Breath n | VV max | 0 | 0 | 0 | 0 |
| | Breath 1 | | 0 | 0 | 0 | 0 |
| | Breath 2 | | 0 | 0 | 0 | 0 |
| | | | 0 | 0 | 0 | 0 |
| | Breath n | | 0 | 0 | 0 | 0 |
| 15 min | | | | | | |

*FIG. 6*

|  | EQCO2 | | ETCO2 | | O2 Pulse | | V.E.Slope | |
|---|---|---|---|---|---|---|---|---|
|  | Average Value | Deviation (%) | Average Value | Deviation (%) | Average Value | Deviation (%) | Average Value | Deviation (%) |
| AV min | 0 | 0 | 0 | 0 | 0 | 0 | 0 | 0 |
| AV ave | 0 |  | 0 | 0 | 0 | 0 | 0 | 0 |
| AV max | 0 | 0 | 0 | 0 | 0 | 0 | 0 | 0 |
| VV min | 0 | 0 | 0 | 0 | 0 | 0 | 0 | 0 |
| VV ave | 0 | 0 | 0 | 0 | 0 | 0 | 0 | 0 |
| VV max | 0 | 0 | 0 | 0 | 0 | 0 |  |  |
|  | 102 | 104 | 102 | 104 | 102 | 104 | 102 | 104 |

FIG. 7

|  | EQCO2 | | | ET CO2 | | | O2 Pulse | | | V.E. Slope | | | Average of Totals | | |
|---|---|---|---|---|---|---|---|---|---|---|---|---|---|---|---|
|  | Rank | D% | S% | Rank | D% | S% | Rank | D% | S% | Rank | D% | S% | Rank | D% | S% |
| AV min | 75 | 12 | 5 | 75 | 14 | 8 | 100 | 4 | 6 | 50 | 9 | 6 | 75 | 9.75 | 6.25 |
| AV ave | 100 | 0 | 0 | 100 | 8 | 0 | 75 | 12 | 0 | 100 | 16 | 0 | 93.75 | 9 | 0 |
| AV max | 50 | 4 | 10 | 50 | 8 | 16 | 50 | 7 | 4 | 75 | 11 | 2 | 55.25 | 7.5 | 8 |
| VV min | 0 | 0 | 0 | 0 | 0 | 0 | 0 | 0 | 0 | 0 | 0 | 0 | | | |
| VV ave | 0 | 0 | 0 | 0 | 0 | 0 | 0 | 0 | 0 | 0 | 0 | 0 | | | |
| VV max | 0 | 0 | 0 | 0 | 0 | 0 | 0 | 0 | 0 | 0 | 0 | 0 | | | |

*FIG. 8*

METHOD OF OPTIMIZING PATIENT OUTCOME FROM CARDIAC RESYNCHRONIZATION THERAPY

CROSS REFERENCE TO CO-PENDING PROVISIONAL APPLICATION

This application claims the benefit of Provisional Application No. 60/453,938, filed Mar. 12, 2003, the entire content of which is hereby incorporated by reference in this application.

BACKGROUND OF THE INVENTION

I. Field of the Invention

The present invention relates generally to the field of cardiac resynchronization therapy (CRT), and more specifically, to a method for optimizing the patient outcome from such therapy. The disclosed method enables physicians to improve the process of implanting and programming biventricular pacemakers/ICDs.

II. Related Art

Biventricular pacing has been recently FDA approved as a new indication of pacemaker therapy for the "resynchronization" treatment of heart failure (HF) patients with wide QRS complex on ECG (ventricular dysynchrony) or abnormal ventricular activation. Although biventricular pacing has been shown to improve HF patient morbidity or their quality of life (QOL), there has been limited success in demonstrating its effect on HF patient mortality. Several problems exist in all phases of CRT:

Implantation: Lead placement on the left ventricle is very important to optimize the right ventricular to left ventricular activation sequence, in particular the activation sequence of the left ventricle (LV), in order to facilitate wall motion and ejection fraction of the ventricle. Currently, most LV electrodes are placed transvenously via the coronary sinus and great veins to a more distal and lateral-basal portion of the left ventricle. Some LV electrode positions may be more anterior or posterior. Echocardiography has been used to assess the degree of resynchronization with respect to the sequence and timing of segmental wall motion activation and stroke volume changes prior to and after implant of the biventricular pacemaker system. The use of echocardiographic measurements during implanting of the left ventricular lead/electrode is difficult to accomplish. Echo measurements are often difficult to duplicate due to positioning of the echo probe, the assessment of diastolic function itself, and are also dependent upon expensive equipment and the requisition of experienced echo stenographers. In addition, many pacemaker follow-up centers may not have readily available, a well trained echocardiography staff. Additionally, the need to enter into a draped, sterile field area of the patient during the implant procedure is problematic.

Delay Programming: Appropriate timing between atrial and ventricular contraction is necessary to optimize ventricular filling and stroke output. Pacemaker manufacturers provide only recommended values for atrial-ventricular (AV) and interventricular (RV-LV or VV) delays that are supported by case studies or clinical studies. These are deficient because they have not been supported by any activity or exercise hemodynamic and pulmonary measurements, other than, perhaps, echo assessment at rest. Aside from resting echo measurements, there does not exist a reliable and simple technique to acutely and chronically assess the efficacy of programmed AV and VV delays. In general, some other method or approach is needed to optimize the delay values on a "per-patient" basis without programming "guesstimate" values recommended by the various pacemaker manufacturers.

DEFINITIONS OF TERMS

The following contains definitions and explanations of certain terms as used in the present context.

End-Tidal Partial Pressure of $CO_2$ ($PetCO_2$, $ETCO_2$)—The partial pressure of carbon dioxide at the end of expiration, or the highest value of $PCO_2$ during a single expiration.

Forward Pump Function—Refers to the ability of the heart to contract and eject blood which has returned to the heart during its relaxation, or filling, cycle via the aorta against a given amount of resistance, or afterload.

Oxygen Pulse ($O_2$ Pulse)—$O_2$ Pulse is an indirect index of combined cardiopulmonary oxygen transport. It is calculated by dividing oxygen uptake (ml/min) by heart rate. In effect, $O_2$ Pulse is equal to the product of stroke volume and arteriovenous $O_2$ difference. Thus circulatory adjustments that occur during exercise, that is, widening arteriovenous $O_2$ difference, increased cardiac output, and redistribution of blood flow to the working muscle, will increase $O_2$ Pulse. Maximal $O_2$ pulse is higher in fitter subjects, lower in the presence of heart disease, and, more importantly, higher at any given workload in the fitter or healthier individual. On the other hand, $O_2$ Pulse will be reduced in any condition that reduces stroke volume . . . ." V. Froelicher, J. Myers, et al., Exercise and the Heart. Mosby-Year Book, Inc. 1993, p.38

Retrograde Pump Function—Refers to the filling of the heart during the relaxation part of the cardiac cycle. Filling pressure and the volume of blood that returns to the heart during diastole are termed preload. Any forward pump failure of the heart can increase the preload on the heart to undesirable levels which, in turn, has an adverse retrograde effect on gas exchange in the lung.

Ventilation-Perfusion Coupling—"For gas exchange to be most efficient, there must be a precise match, or coupling, between ventilation (the amount of gas reaching the alveoli) and perfusion (the blood flow in pulmonary capillaries). Changes in the $PCO_2$ within the alveoli cause changes in the diameters of the bronchioles. Passageways servicing areas where alveolar carbon dioxide levels are high dilate, allowing carbon dioxide to be eliminated from the body more rapidly; those servicing areas where the $PCO_2$ is low constrict. As a result of the modifications these two systems (also for $PO_2$), alveolar ventilation and pulmonary perfusion are always synchronized. Poor alveolar ventilation results in low oxygen and high carbon dioxide levels in the alveoli; consequently, the pulmonary capillaries constrict and the airways dilate, bringing airflow and blood flow into closer physiological match. High oxygen and low carbon dioxide alveolar partial pressures cause constriction of the respiratory passageways and a flushing of blood into the pulmonary capillaries. At all times, these homeostatic mechanisms provide the most appropriate conditions for efficient gas exchange." E. Marieb, Human Anatomy and Physiology. Benjamin/Cummings Publishing Company, 1992, p.749

Ventilatory Efficiency Slope (of Ventilation vs. $VCO_2$)—The recorded test data contain the channels minute ventilation VE and carbon dioxide output $VCO_2$ as time series with sample points (moments of time) $t_i$, so there are two sets of data points $VE_i$ and $VCO_{2i}$ with i-1, . . . , N. To find the best straight line fit $VE=\alpha VCO_2+b$ to the ensemble of point pairs ($VE_i$, $VCO_{2i}$) one can use the linear regression analysis minimizing the sum of squares of distances of these points to a straight line, see for instance PRESS, W. H., B. P. FLANNERY, S. A. TEUKOLSKY, W. T. VETTERLING:; Numerical Recipes, The Art of Scientific Computing. Cambridge University Press, Cambridge etc., 1986, Chapter 14.2. The main results of such an analysis are the constants α and b describing the regression line and the regression coefficient r as a measure for the regularity of data lying along and around this line. The constant α is the VE to $VCO_2$ slope, or ventilatory efficiency slope, of the above mentioned data ensemble.

Ventilatory Equivalent for carbon dioxide ($VE/VCO_2$, $EQCO_2$)—The $EQCO_2$ is calculated by dividing ventilation (L/min) by $VCO_2$ (L/min). "$VE/VCO_2$ represents the ventilatory requirement to eliminate a given amount of $CO_2$ produced by the metabolizing tissues. Since metabolic $CO_2$ is a strong stimulus for ventilation during exercise, VE and $VCO_2$ closely mirror one another, and after a drop in early exercise, $VE/VCO_2$ normally does not increase significantly throughout sub-maximal exercise. However, in the presence of chronic heart failure, $VE/VCO_2$ is shifted upward compared to normals, and high $VE/VCO_2$ values are one of the characteristics of the abnormal ventilatory response to exercise in this condition." Ibid Froehlicher.

SUMMARY OF THE INVENTION

The present invention, to a large extent, obviates the problems discussed in the foregoing for each of the phases described above. The physiology supportive of the present invention involves the relationship of the pulmonary circulation and gas exchange in the lungs that will readily reflect upon ventricular filling pressures, pulmonary venous flow, and ventilation to perfusion matching in the lungs (see also Definitions). A sound physiologic basis exists to support the theory that the oxygen pulse ($O_2$ Pulse), end-expired, partial pressure of $CO_2$ ($ETCO_2$), and ventilatory equivalents of $CO_2$ ($EQCO_2$) are key parameters to assess pump function of the heart and the efficiency of gas exchange in the lungs. Any therapy, which reduces stroke output of the heart, may cause a volume load on the heart, thus affecting the pulmonary venous blood flow gradient and ventilation to perfusion matching in the lungs. When ventilation to perfusion is mismatched, the $ETCO_2$ and $O_2$ Pulse will be reduced and $EQCO_2$ will be increased. Because gas exchange measurements are made on a "breath-by-breath" basis, physiologic changes resulting from altering lead placement during implantation or changes in delay programming made post-implantation are observable more or less instantaneously, thus they can be used to guide the decision making process in either case.

Optimum Lead Implantation: The present invention describes a noninvasive assessment of global LV pump function (stroke volume) simultaneously with the filling of the heart with respect to relative effects on pulmonary gas exchange. In other words, noninvasive, breath-by-breath measurements are made of both forward pump function as well as retrograde effects on filling pressures, pulmonary venous flow, and gas exchange at the alveolar/capillary membrane interface. The most ideal LV electrode position during implanting of the biventricular pacing system is obtained by monitoring of the patient's $O_2$ Pulse, $EQCO_2$, and, optionally, $ETCO_2$. The optimal lead placement will result in the highest $ETCO_2$ and $O_2$ Pulse values and lowest $EQCO_2$ values. An additional benefit is that the methodology can eliminate the disadvantage of echocardiography previously cited in that the measurement can be made out of the sterile field and is capable of assessing both preload and global ejection properties of the heart.

Optimal Delay Programming: Assessment of the most effective AV and VV delays is more meaningful when the heart is subjected to an acute change in volume load, as is the case during mild treadmill exercise with an augmented venous return. An "acute assessment" of any combination of AV delay or VV delay that are programmed is obtained by monitoring of the patient's $ETCO_2$, $O_2$ Pulse, $EQCO_2$, and the ventilatory efficiency slope during low level (5% elevation, 2 miles/hr speed) steady state exercise. The most optimally programmed AV and interventricular delays will result in the highest expired $ETCO_2$ and $O_2$ Pulse values and the best ventilation efficiency (lowest slope) and lowest $EQCO_2$ during mild, "sub-AT" exercise. The measurement system utilizes noninvasive, breath-by-breath gas exchange methods that provides amplified "on-line" recording of the above parameters. These parameters are measured at predetermined values of AV and VV delay, each are described quantitatively and qualitatively, and the resulting measurements are displayed to improve or optimize the efficacy of CRT. Optionally, the measurements and the optimization algorithms can be incorporated into the pacemaker programmer system itself. The online system will not only have the specificity but will have the sensitivity to "fine tune" the biventricular pacing system in accordance with gas exchange efficiency in the lungs and also directly correlate to stroke volume, the oxygen pulse.

The measurements will differ for each patient, reflecting the fact that each patient has unique cardiac and pulmonary function.

BRIEF DESCRIPTION OF THE DRAWINGS

In the drawings:

FIG. 2 is a schematic drawing that illustrates the functional components of a cardiac resynchronization system;

FIG. 4 illustrates a Boundary Conditions Table for a particular bi-ventricular pacemaker;

FIG. 5 illustrates an AV/VV Optimization Protocol example showing when particular tasks occur;

FIG. 6 illustrates the organization of the measured data once it is acquired during the example Optimization Protocol;

FIG. 7 illustrates the organization of Intermediate Data after each two-minute segment of the example Optimization Protocol;

FIG. 8 illustrates the organization of a Decision Matrix and sample values for the calculated results;

DETAILED DESCRIPTION

Figure 1:
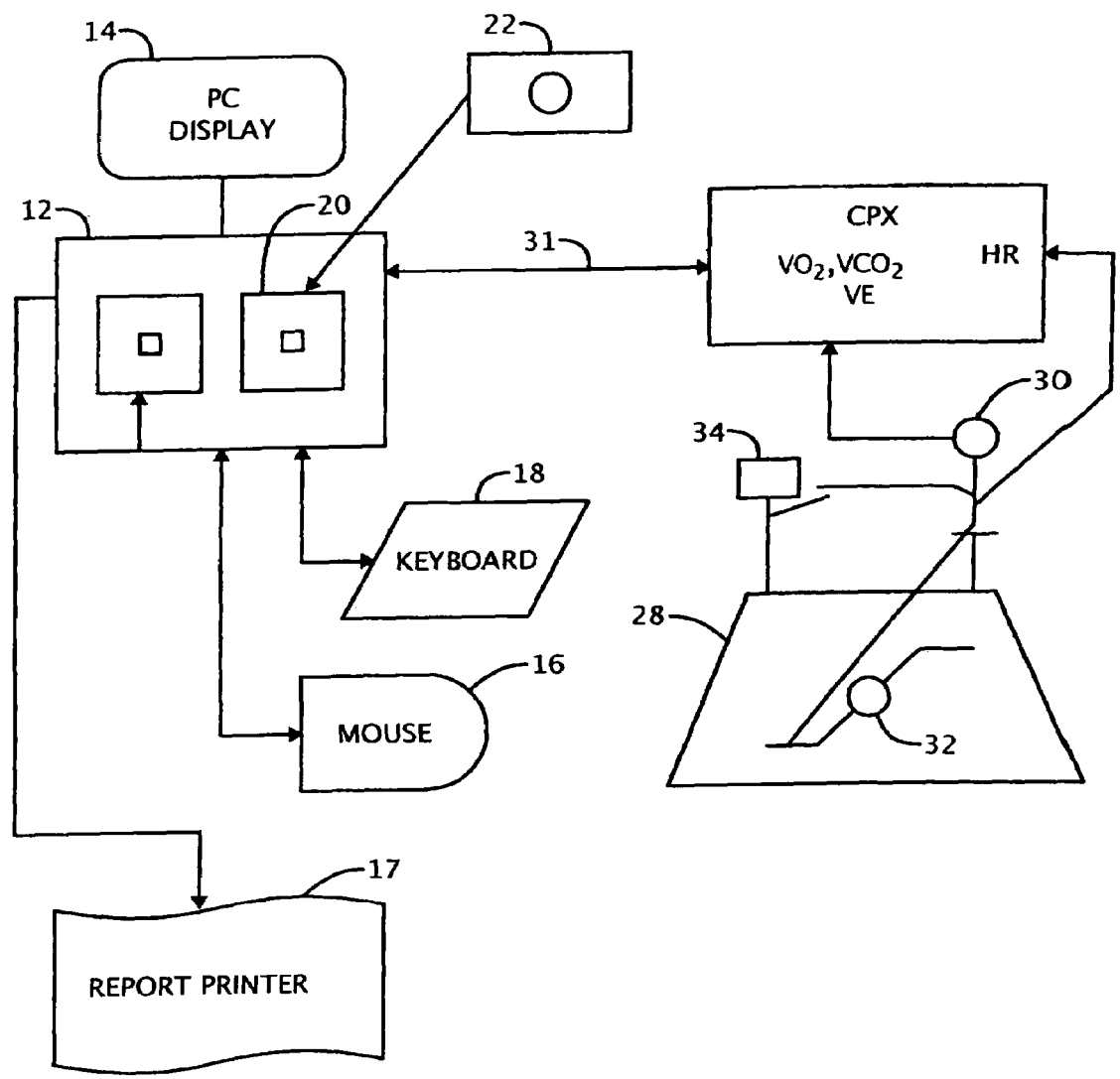
FIG. 1 is a schematic block diagram drawing that illustrates the functional components of a CPX testing system usable with the present invention.

The following detailed description with respect to patient data is intended to be exemplary of a preferred method of utilizing the concepts of the present invention and is not intended to be exhaustive or limiting in any manner with respect to similar methods and additional or other steps which might occur to those skilled in the art. The following description further utilizes illustrative examples, which are believed sufficient to convey an adequate understanding of the broader concepts to those skilled in the art, and exhaustive examples are believed unnecessary.

General Considerations—The present invention is not intended to make decisions, but rather to provide information to guide the decision making process by the physician. In doing so, decisions regarding lead placement (is one location on the heart better than another location?) and programming choices (is AV delay setting better than other choices of delay setting) can be made. In some cases, the answer to these questions may be no—there is no clear reason to use one choice over another. Even in this case, the decision making process described in the present invention is an improvement over a process devoid of specific, sensitive data. In the present invention, specificity is provided by a quantitative analysis of response variables that are based upon well known, proven measurements of human physiology. Sensitivity is supported by qualitative assessments of the measurements themselves.

The general class of data utilized in the present invention, dynamic-cardiopulmonary (DCP), is obtained 1) at rest during the implantation procedure and 2) during physical exercise testing performed in accordance with a standardized workload protocol as the forcing function to elicit physiologic changes resulting from increasing amounts of workload. In both cases, such data can be viewed as an "acute" evaluation of the primary "endpoint" to gauge the effect of biventricular pacing on hemodynamic and pulmonary performance and on left ventricular stroke volume. When measured during exercise (2) the data further describes how an individual is able to function in the physical world in terms of the physiologic changes that the individual experiences when engaged in the performance of physical work. A further "acute" assessment of CRT is performed during exercise by selectively modifying the atrial-ventricular timing and interventricular (VV) delays to determine the optimal such timing delays.

The physiologic changes are measured using a cardiopulmonary exercise testing system (CPX) to measure selected variables associated with expired oxygen, carbon dioxide, ventilation, and heart rate. In theory, certain benefits derived from the present invention could be implemented using only a carbon dioxide analyzer equipped with a means for displaying the expired $CO_2$ waveform. However, because of the requirement for measuring "forward" pump function, both heart rate and oxygen consumption, per breath, are needed to measure $O_2$ Pulse. Consequently, a carbon dioxide analyzer alone is insufficient.

During the acute phase of evaluation, the dependent variables, $ETCO_2$, $EQCO_2$, $O_2$ Pulse, and the ventilatory efficiency slope, are measured during steady-state conditions, either at rest or at a constant workload. In the present invention, the independent variables are 1) lead location, and 2) the AV and VV delay values. Thus, changes made by the physician to an independent variable have the effect of changing the ventricular filling and stroke output of the heart that, in turn, alters the ventilation-perfusion coupling. As local hemodynamic and pulmonary regulatory mechanisms response to altered LV electrode position or AV and VV intervals, the selected dependent variables rapidly change, are measured, and the measured values automatically scaled and displayed to provide visual feedback to the physician during lead implantation and AV/VV delay evaluation. In doing so, a physician is provided with a true, physiologic assessment of the patient's condition resulting from changes made to an independent variable at any point in time during the procedure.

The data gathering aspect of the invention involves known techniques and analyses and it is the aspects of processing, combining, and presenting the data in which the invention enables an observer to gain new and valuable insight into the present condition and condition trends in patents. Thus, in accordance with the preferred method, a dynamic cardiopulmonary analysis is displayed for each data set. The performance of such a test is well understood by individuals skilled in the art, and no further explanation of this, except for the AV/VV delay optimization protocol, is believed necessary.

Equipment—With this in mind typical hardware is shown in FIG. 1, which illustrates typical equipment whereby a cardiopulmonary exercise test (CPX) may be conducted and the results displayed in accordance with the method of the present invention. The system is seen to include a data processing device, here shown as a personal computer or PC 12, which comprises a video display terminal 14 with associated mouse 16, report printer 17 and a keyboard 18. The system further has a floppy disc handler 20 with associated floppy disc 22. As is well known in the art, the floppy-disc handler 20 input/output interfaces comprise read/write devices for reading prerecorded information stored, deleting, adding or changing recorded information, on a machine-readable medium, i.e., a floppy disc, and for providing signals which can be considered as data or operands to be manipulated in accordance with a software program loaded into the RAM or ROM memory (not shown) included in the computing module 12.

The equipment used in the exercise protocol includes either a bicycle ergometer or treadmill designed for use in a cardiopulmonary stress testing system (CPX) as is represented at 28 together with a subject 30 operating a pedal crank input device 32 of the ergometer. A graphic display device 34 interfaces with the subject during operation of the CPX device The physiological variables may be selected from heart rate (HR), ventilation (VE), rate of oxygen uptake or consumption ($VO_2$) and carbon dioxide production ($VCO_2$) or other variables derived from these basic measurements. Physiological data collected is fed into the computing module 12 via a conductor 31, or other communication device.

The equipment used in cardiac resynchronization therapy is illustrated in FIG. 2, and includes the cardiac resynchronization device (40) and lead system (42). Typically, implantation is done under local anesthesia with the patient sedated. Three leads are implanted: transvenous pacing leads are placed in the right atrium (44) and right ventricle (46), and a third transvenous left ventricle lead (48) is inserted into a distal cardiac vein via the coronary sinus. The goal is to place this third lead on the left ventricular freewall in a mid-cardiac position with good physical and electrical separation from the RV lead. This separation helps to optimize resynchronization to correct the ventricular contraction pattern. Also shown in FIG. 2 is a pacemaker programmer (50), used to program and evaluate the timing characteristics of the pacemaker.

It should be noted that either a PC (12) or pacemaker programmer (50) could be used to acquire the measurements and process those measurements to implement the present invention. Therefore, the further detailed description of the present invention will be made independent of the type and characteristics of the data processing means.

Acute Assessment—Optimal Lead Placement During Implantation

The present invention provides a feedback mechanism to gauge the effectiveness of the placement of the left ventricular and right ventricular leads. As stated above, the goal of placement of these leads is to provide good physical and electrical separation. Achievement of this goal is complicated by the mechanical challenges in lead placement itself and by the presence of necrotic tissue on the surface of the heart, which has a higher electrical resistance than normal cardiac tissue. While cardiac ultrasound can be helpful in providing feedback to the implanting physician regarding the changes in sequence of ventricular wall motion activation, it has limited use in assessing pulmonary function. Since the main objective of cardiac resynchronization itself is improved hemodynamic and pulmonary performance, the present invention provides a direct measurement of hemodynamic and pulmonary performance that can be used in real-time to evaluate if the lead placement goal is optimally reached. The present invention describes a noninvasive assessment of global LV pump function (stroke volume) concomitantly with the filling of the heart with respect to relative effects on pulmonary gas exchange.

In other words, noninvasive, breath-by-breath measurements are made of both "forward" pump function as well as "retrograde" effects on filling pressures, pulmonary venous flow, and gas exchange at the alveolar/capillary membrane interface. The measurement system utilizes non-invasive, breath-by-breath gas exchange methods that provides amplified "on-line" recording of the above parameters.

Figure 3:
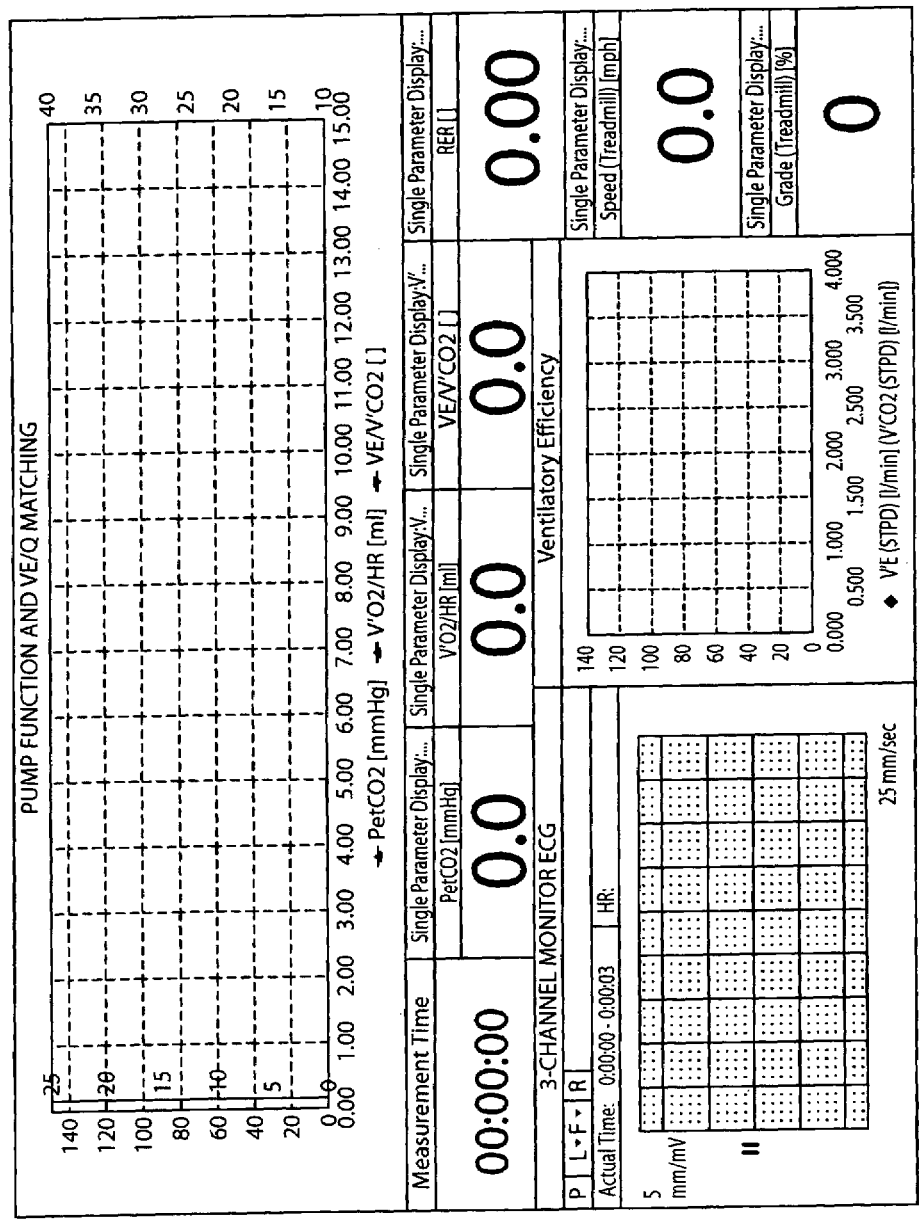
FIG. 3 illustrates a data display viewed by a physician while acquiring data using the present invention.

The most ideal LV electrode position during implanting is obtained by monitoring of the patient's $O_2$ Pulse, $EQCO_2$, and, optionally, $EQCO_2$ during the procedure of placing the LV and RV electrodes. The optimal lead placement will result in the highest $ETCO_2$ and $O_2$ Pulse values and lowest $EQCO_2$ values. This can be determined on a relative basis for different lead locations using a display of these variables as shown in FIG. 3 Variable Display.

Acute Assessment—Optimal Delay Programming

With left ventricular conduction disease, cardiac resynchronization improves hemodynamic and pulmonary performance by forcing the left ventricle to complete contraction and begin relaxation earlier, which can increase filling time. While it is assumed that simultaneous activation of the ventricles and septum results in improved left ventricular stroke volume, cardiac resynchronization systems offer the ability to alter the delay in ventricular activation. Additional such delay programming is provided for atrial-ventricular activation. What is not provided is a method to assist the physician in selecting the optimum delay values for either to achieve the main objective of CRT—improved hemodynamic and pulmonary performance for individual patients.

The present invention further provides a computer assisted optimizing process using the same measurements described for optimizing lead placement. Assessment of the most effective AV (paced or sensed) and VV delays is more meaningful when the heart is subjected to an acute change in volume load, as is the case during mild treadmill exercise with an augmented venous return. An "acute assessment" of any combination of AV delay or VV delay that can be programmed is obtained by monitoring of parameters indicative of the patient's "forward" pump function or stroke volume output, as well as "retrograde" effects on filling pressures, pulmonary venous flow, and gas exchange at the alveolar/capillary membrane interface. This acute assessment is performed on the patient during low level (5% elevation, 2 miles/hr speed) steady state treadmill exercise. The best choices are $O_2$ Pulse for "forward" pump function and $EQCO_2$ for "retrograde" effects. However, in order to further refine the selection process, additional measurements such as the linear ventilatory efficiency slope [Minute Ventilation (VE) to expired Carbon Dioxide ($VCO_2$) slope] and $ETCO_2$ can be included. The most optimally programmed AV and interventricular delays will result in the highest expired $ETCO_2$ and $O_2$ Pulse values and the best ventilation efficiency (lowest linear slope) and lowest $EQCO_2$ during mild, "sub-AT" exercise.

These parameters are measured at pre-determined values for AV and VV delay, as defined in the table identified in FIG. 4 as Boundary Conditions. A unique table of Boundary Conditions is established for each manufacturer of CRT systems, and the size of the table, in terms of number of rows and number of columns, can be adjusted to accommodate many different such devices. In the example provided in FIG. 4, three values of AV delay are stored that correspond to minimum (60), average (62), and maximum (64) delay values allowable by the CRT system. Similarly, three values of VV delay are stored that correspond to the minimum (66), average (68), and maximum (70) delay values allowable by the CRT system. To expedite the procedure, the data collection phase is divided into two, sessions of 6–9 minutes while the patient is walking on a treadmill programmed for 5% elevation at a speed of 2 miles/hour (FIG. 5—AV/VV Delay Optimization Protocol). In the example provided in FIG. 5, during the first 6 minutes of steady-state exercise, the three values of AV delay are sequentially programmed into the pacemaker every two minutes. This programming is accomplished manually by placing the programming wand over the implanted device on the patient's chest and selecting a delay setting corresponding to each value of AV delay stored in the Boundary Conditions table. After zeroing all entries, all measured data for each breath during the two-minute collection period associated with each of the three delay values is stored into the tables at 82 in FIG. 6—Stored Data Sets.

Upon completion of each of the two-minute data collection periods, the central tendency and deviation percentage of each measured variable is computed and, after zeroing all entries, stored in an Intermediate Table as described in FIG. 7. Only data for breaths recorded during the last one and one-half minutes of each collection period is used in the calculations. Such computations of central tendency can include, but is not limited to, the simple arithmetic average, as at 102 in FIG. 7 for example. The Deviation % as in 104 is first calculated by summing, for each breath in the 1.5-minute calculation period, the absolute value of the difference between the average value 102 and the recorded value. This total is then divided by the product of the number of breaths in the calculation period times the average value 102. Multiplying this calculation by 100 yields the Deviation % 104. The Deviation % is intended to provide a qualitative assessment of the "tightness" of the data sets. In other words, a small Deviation % is indicative of low variability of the data in each set, hence a high-quality test. A large value of Deviation % would indicate unwanted patient events (coughing, for example) or possibly unwanted physiologic consequences (Cheyne-Stoke breathing patterns, for example).

Upon completion of the first 6 minutes of data collection, further processing of the data stored in the Intermediate Table is performed. The Decision Matrix as in the example shown in FIG. 8 is first zeroed, and the following steps are taken to calculate the values for each row and column.

Step 1—Assign Rank—The Rank value is intended to provide a qualitative assessment of the optimal choice for either AV delay or VV delay. First, the highest average value for $O_2$ Pulse and $ETCO_2$ and the lowest average value for $EQCO_2$ and Ventilatory Efficiency slope are identified. A Rank value of 100 is assigned to the corresponding position in the Decision Matrix for each such determination. For example, if the highest value found in column 2, rows 3–5, in FIG. 7 was at row 4, or AV ave, then 100 is assigned in FIG. 8 to column 2 in the row defined as AV ave. The associated value for Deviation % found in FIG. 7 is also stored in the next column in the same row of FIG. 8. Next, the lowest average value for $O_2$ Pulse and $ETCO_2$ and the highest average value for $EQCO_2$ and V.E. slope are identified. A Rank value of 50 is assigned to the corresponding position in the Decision Matrix for each such determination. For example, if the lowest value found in column 2, rows 3–5, in FIG. 7 was at row 5, or AV max, then 50 is assigned in FIG. 8 to column 2 in the row defined as AV max. The associated value for Deviation % found in FIG. 7 is also stored in the next column in the same row of FIG. 8. A Rank value of 75 is then assigned to the Rank column in the row for which no entry has been previously made, and the associated value for Deviation % found in FIG. 7 is also stored in the next column is the same row of FIG. 8. In this manner entries will have been made in all columns for the rows identified as AV min, AV ave, and AV max except the S % column and the Average of the Totals.

The next step is to compute, for each row in FIG. 8 identified as AV min, AV ave, and AV max, the Average Total Rank. This is done by summing the individually assigned Rank values for each of the variables in the same row and dividing by 4. The "perfect" Average Rank, then, is 100, which indicates that each variable for that particular setting is in theoretical conformance—the two that should be the highest are the highest and the two that should be the lowest are the lowest.

Step 2 Define Deviation—Similarly, the Average Deviation Percentage is calculated for each such row and stored in the column of that row identified in FIG. 8 as D %.

Step 3—Define Separation—The next step is to compute the values for Separation % for each of the rows in FIG. 8 identified as AV min, AV ave, and AV max. The Separation % value provides a qualitative assessment of the difference, or separation, between the components of Rank (in this example, average value of the variable data set at each AV delay setting). A small value of S % indicates that there is little measured difference between the average values of data sets at each delay setting; hence the test may prove inconclusive. The higher the value of S %, the more conclusive the test results. For each of the columns for each of the variables, a value of 0 is assigned to the S % column in the row having the maximum average Rank. For example, in FIG. 8, the row with the highest average Rank, 93.75, is the row AV ave, consequently, each column identified as S % is set to 0. The values for S % for each column of the remaining, unassigned rows is first computed by subtracting the average value from FIG. 7 for the associated row from the average value from FIG. 7 for the row that has been assigned a value of 0 for S %. The absolute value of this operation is then divided by the average value from FIG. 7 for the row that has been assigned a value of 0 for S %. Multiplying this operation by 100 yields S % for each of the remaining 2 rows, in this example, for each variable. In a similar fashion described to compute average Rank and D %, average S % is computed for each row and stored in the S % column under Average of Totals.

Figure 9:
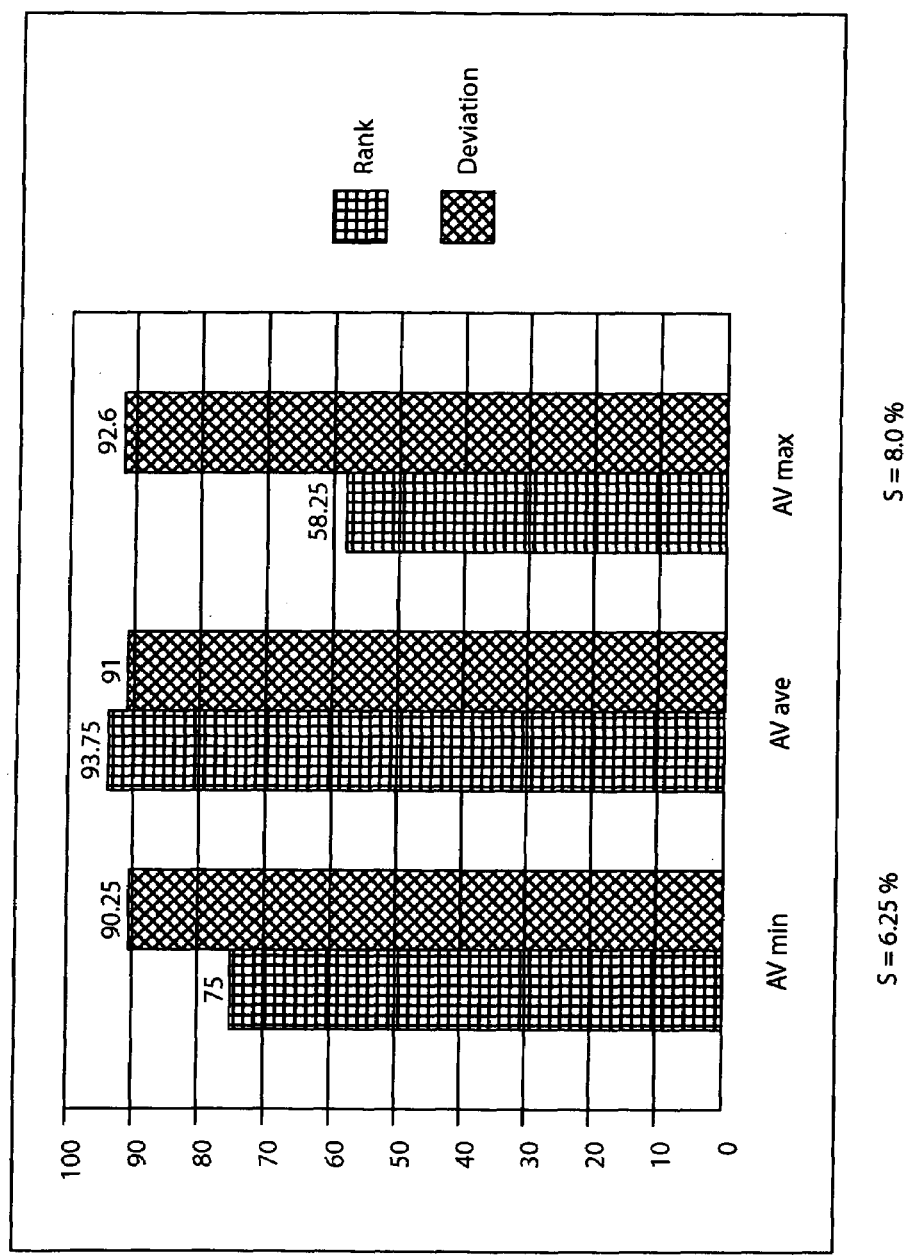
FIG. 9 illustrates a Report Summary in a histogram format for the data used in FIG. 8.

The physician then prints the final report for review at 90 in FIG. 5. The final report consists of a printed version of the Decision Matrix FIG. 8 and a Report Summary, FIG. 9, summarizing the calculations stored in the Decision Matrix in the form of a histogram in this case (any other choice for graphical display is suitable). The Rank bar for each AV setting is placed on a scale with a maximum value of 100. The height of the bar for each setting is then the value of Average Rank from the Decision Matrix for that setting. To match the "bigger is better" assumption for Rank value, the height of the D % bar in FIG. 9 is scaled to a value equal to 100 minus the average D % for each setting. The average S % for the settings with lower average Rank values is printed below their associated setting columns. Thus, the optimal setting is quantified as the setting with the highest average Rank, and this, in turn, can be assessed qualitatively by the relative heights of the Rank columns (equal heights indicate poor quality), average Deviation % (large values indicates poor quality), and Separation % (low value indicates poor quality). During a one-minute (or optionally, longer) period, the physician selects and programs the AV delay value at 92 in FIG. 5 after first inspecting the Decision Matrix FIG. 8 and the Report Summary FIG. 9.

The second 6-minute data collection phase is started. Similarly, each of the VV delays defined in the Boundary Conditions Table FIG. 4 are programmed every two minutes and each of the measured values for each breath is stored into the Stored Data Sets (84) identified in FIG. 6. The entire process described above for selecting AV delay is repeated in detail for selecting VV delay, using instead those rows identified in FIGS. 6, 7, and 8 for VV data storage. After inspecting the Decision Matrix FIG. 8 and the Report Summary FIG. 9 (in this case, showing VV min, VV ave, and VV max), the physician then selects and programs the VV delay value at 96 in FIG. 5.

The invention has been described in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as the equipment details and operating procedures can be accomplished without departing from the scope of the invention itself.

The invention claimed is:

1. A method of optimizing cardiac resynchronization therapy provided to a patient with ventricular dysynchrony including
    (a) non-invasively measuring hemodynamic and pulmonary performance in terms of data representing selected variables indicative of one or more functions selected from the group consisting of forward pump function (stroke volume output), retrograde effects on filling pressures, pulmonary venous flow, and gas exchange at the alveolar/capillary membrane interface during exercise; and
    (b) utilizing said data as representing dependent variables; and adjusting selected pacing parameters including atrial-ventricular (AV) delay and left ventricular-right ventricular (VV) delay.

2. A method as in claim 1 wherein said forward pump function of the heart is derived from a the oxygen pulse ($VO_2$/HR).

3. A method as in claim 2 wherein said retrograde effect on filling pressures, pulmonary venous flow, and gas exchange at the alveolar/capillary membrane interface is derived from the ventilatory equivalent for $CO_2$ (VE/$VCO_2$).

4. A method as in claim 3 including utilizing additional cardiopulmonary variables including end tidal $CO_2$ ($ETCO_2$).

5. A method as in claim 4 including acquiring, collecting and displaying said cardiopulmonary variables during low intensity exercise and storing said variables as data sets, each set being associated with a unique value of atrialventricular (AV) delay and left ventricular-right ventricular (VV) delay.

6. A method as in claim 5 wherein the values for AV and VV delay are defined in a boundary conditions table unique to a pacemaker manufacturer of interest.

7. A method as in claim 5 including utilizing the stored cardiopulmonary variable data sets to assist a physician in selecting the optimal combination of AV and VV delay values from several possible such values as defined in a boundary condition table unique to a pacemaker manufacturer of interest uniquely for individual patients.

8. A method as in claim 7 wherein a single set of equipment is utilized to optimize all phases of cardiac resynchronization therapy, including appropriate rate response during exercise/activity and device programming, including dynamic AV and VV delay of which resting AV and VV delay are a portion thereof.

9. A method as in claim 7 wherein decisions can be made from quantitative and qualitative information.

10. A method as in claim 5 including selection of an optimal combination of AV and VV delay values using the following:
  (a) executing an AV/VV delay optimization protocol defining a time schedule for system operator tasks and data processing tasks for each unique value of AV and VV delay as defined in a boundary condition table unique to a pacemaker manufacturer of interest;
  (b) storing variable values measured for each breath during the delay optimization protocol into a Stored Data Sets table for subsequent analysis;
  computing and storing a central tendency and percent deviation from the central tendency for each measured variable in each data set obtained immediately after collection into an Intermediate table for subsequent analysis;
  (d) computing and storing into a Decision Matrix ranking, values for quantifying the response to changes in AV and VV delay settings using the values obtained in;
  (e) computing and storing into a Decision Matrix, deviation indices to provide a qualitative assessment of the variability of the data sets used to compute the ranking values obtained in (d);
  (f) computing and storing into a Decision Matrix, separation indices to provide a qualitative assessment of the magnitude of the difference between the central tendencies of the data sets used to calculate the ranking values in (d);
  (g) printing a report of the Decision Matrix with all values used to compute average rank, deviation, and separation in (d), (e), and (f);
  (h) printing a graphical report in the form of a histogram having two juxtaposed bars—one bar representing the ranking values determined in (d), and another bar representing the average deviation % computed from (e)—and the separation indices computed in (f); and
  (i) programming AV and VV delay values that provide the best forward pump function and the best retrograde effect on filling pressures, pulmonary venous flow, and gas exchange at an alveolar/capillary membrane interface using quantitative and qualitative data computed in (a) through (h).

11. A method as in claim 10 wherein the variables computed in (a) to (f) are represented in other common graphical formats selected from the group consisting of lines, bars, and pie charts.

12. A method as in claim 1 wherein said retrograde effect on filling pressures, pulmonary venous flow, and gas exchange at the alveolar/capillary membrane interface is derived from the ventilatory equivalent for $CO_2$ ($VE/VCO_2$).

13. A method as in claim 1 including utilizing additional cardiopulmonary exercise variables including end tidal $CO_2$ ($ETCO_2$).

14. A method as in claim 1 including utilizing additional cardiopulmonary variables selected from the group consisting of end tidal $CO_2$ ($ETCO_2$), and ventilatory equivalents ($VE/VCO_2$).

15. A method as in claim 1 wherein said data representing selected variables are measured under steady-state conditions and are treated as dependent variables for the purposes of selection of the optimal combination of AV and VV delay values which are independent variables.

16. A method as in claim 1 wherein a single set of equipment is utilized to optimize all phases/aspects of cardiac resynchronization therapy, including appropriate rate response during exercise/activity and device programming, including dynamic AV and VV delay of which resting AV and VV delay are a portion thereof.

17. A method as in claim 1 including measuring retrograde effects using an end-tidal $CO_2$ analysis.

* * * * *

UNITED STATES PATENT AND TRADEMARK OFFICE
CERTIFICATE OF CORRECTION

| | | |
|---|---|---|
| PATENT NO. | : 7,225,022 B2 | Page 1 of 1 |
| APPLICATION NO. | : 10/797948 | |
| DATED | : May 29, 2007 | |
| INVENTOR(S) | : Stephen T. Anderson and Dean J. MacCarter | |

It is certified that error appears in the above-identified patent and that said Letters Patent is hereby corrected as shown below:

In column 11, line 35, before "computing", insert --(c)--;

In column 11, line 42, after "in", insert --(c)--.

Signed and Sealed this

Tenth Day of July, 2007

JON W. DUDAS
*Director of the United States Patent and Trademark Office*